US011660471B2

(12) United States Patent
Miyazaki et al.

(10) Patent No.: US 11,660,471 B2
(45) Date of Patent: May 30, 2023

(54) RADIATION THERAPY SYSTEM

(71) Applicants: Hitachi, Ltd., Tokyo (JP); NATIONAL UNIVERSITY CORPORATION HOKKAIDO UNIVERSITY, Sapporo (JP)

(72) Inventors: Koichi Miyazaki, Tokyo (JP); Naoki Miyamoto, Sapporo (JP)

(73) Assignees: HITACHI, LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 408 days.

(21) Appl. No.: 16/200,682

(22) Filed: Nov. 27, 2018

(65) Prior Publication Data

US 2019/0175941 A1  Jun. 13, 2019

(30) Foreign Application Priority Data

Dec. 7, 2017 (JP) .............................. JP2017-235206

(51) Int. Cl.
*A61N 5/10* (2006.01)
*A61B 6/00* (2006.01)
*A61B 90/00* (2016.01)

(52) U.S. Cl.
CPC .......... *A61N 5/1049* (2013.01); *A61B 6/4014* (2013.01); *A61B 6/487* (2013.01);
(Continued)

(58) Field of Classification Search
None
See application file for complete search history.

(56) References Cited

U.S. PATENT DOCUMENTS

2010/0067660 A1* 3/2010 Maurer, Jr. ............ A61B 6/541
378/95
2010/0215149 A1* 8/2010 Takemoto ........ A61B 17/12113
378/98
(Continued)

FOREIGN PATENT DOCUMENTS

JP  2012-501792 A  1/2012
JP  2015-016161 A  1/2015
(Continued)

OTHER PUBLICATIONS

Extended European Search Report received in corresponding European Application No. 18208264.4 dated Mar. 26, 2019.

*Primary Examiner* — Shahdeep Mohammed
(74) *Attorney, Agent, or Firm* — Mattingly & Malur, PC

(57) ABSTRACT

The present invention makes it possible to provide a radiation therapy system capable of not only inhibiting treatment time from increasing more effectively than before but also reducing the loads of fluoroscopic radiation photographing apparatuses. The radiation therapy system has: a therapeutic radiation irradiation apparatus to irradiate a target with therapeutic radiation; two fluoroscopic radiation photographing apparatuses to photograph the target simultaneously from two directions; a target position computation apparatus to compute a three-dimensional position of the target on the basis of photographed fluoroscopic images; a therapeutic radiation irradiation control apparatus to control the irradiation of the therapeutic radiation on the basis of the computed three-dimensional position of the target; and a fluoroscopic radiation photographing control apparatus to control irradiation quantities per unit time of the fluoroscopic radiation photographing apparatuses on the basis of the three-dimensional position of the target.

5 Claims, 10 Drawing Sheets

(52) U.S. Cl.
CPC .......... *A61B 6/5217* (2013.01); *A61N 5/1067* (2013.01); *A61N 5/1077* (2013.01); *A61B 6/54* (2013.01); *A61B 2090/376* (2016.02); *A61N 2005/1061* (2013.01); *A61N 2005/1074* (2013.01)

(56) References Cited

U.S. PATENT DOCUMENTS

| | | | | |
|---|---|---|---|---|
| 2013/0083895 | A1* | 4/2013 | Umekawa | A61B 6/542 378/62 |
| 2015/0018595 | A1* | 1/2015 | Taguchi | A61N 5/1067 600/1 |
| 2015/0036793 | A1* | 2/2015 | Umekawa | A61N 5/1049 378/8 |
| 2015/0190657 | A1 | 7/2015 | Maurer, Jr. et al. | |

FOREIGN PATENT DOCUMENTS

| | | | |
|---|---|---|---|
| JP | 2016-106756 | * | 6/2016 |
| JP | 2016-106756 W | | 6/2016 |

\* cited by examiner

RADIATION THERAPY SYSTEM

BACKGROUND

The present invention relates to a radiation therapy system to recognize the position of a target in a test object in real time and irradiate the target with therapeutic radiation.

The general technologies in this technological field are described in Japanese Unexamined Patent Application Publication (Translation of PCT Application) No. 2012-501792 and Japanese Unexamined Patent Application Publication No. 2015-016161.

Japanese Unexamined Patent Application Publication (Translation of PCT Application) No. 2012-501792 describes that "An image guided treatment is performed in order to treat a target. Measurement data representing the movement of the target are obtained in order to perform the image guided treatment. One or more timings of X-ray images are decided on the basis of the measurement data. The treatment is applied to the target by using a position of the target."

Further, Japanese Unexamined Patent Application publication No. 2015-016161 describes that "A plurality of first irradiation units, a plurality of detection units, a judgment unit, and a control unit are provided. The irradiation units irradiate a test object with radiations respectively. The detection units detect radiations transmitted through the test object and generate images on the basis of the detected radiations, respectively. The judgment unit judges whether or not a target in the interior of the test object is included in a first region by using a predetermined image that is any one of the multiple images. The control unit controls the first irradiation units so that the irradiation quantities of the radiations per unit time may be smaller when the target is not included in the first region than when the target is included in the first region."

SUMMARY

In radiation therapy, a diseased part (target) such as a cancer is irradiated with a charged particle beam such as an electron beam, a proton beam, or a carbon beam or a therapeutic radiation such as X-rays or γ-rays by using a therapeutic radiation irradiation apparatus.

In highly-accurate radiation therapy in particular, a therapeutic radiation irradiation apparatus is required to be controlled in response to the variation of the position or the shape of a target caused by respiration, heartbeat, or bowel movements. There is real-time image gated radiation therapy as an irradiation method used in highly-accurate radiation therapy.

In the real-time image gated radiation therapy, a three-dimensional position of a target is measured and traced directly or indirectly from a three-dimensional position of a marker placed in a vicinity of the target by irradiating and seeing through the interior of a test object with fluoroscopic radiation from a plurality of directions at predetermined time intervals and a diseased part is irradiated with therapeutic radiation only when the target exists in a predetermined irradiation permission region.

As the fluoroscopic radiation used here, a charged particle beam such as an electron beam, a proton beam, or a carbon beam, X-rays, or γ-rays are named. Radiation for therapy is referred to as "therapeutic radiation" and radiation for measurement is referred to as "fluoroscopic radiation" hereunder in order to distinguish between radiation for therapy and radiation for measuring the position of a target.

Photographing by fluoroscopic radiation for measuring the position of a target is carried out intermittently at a predetermined interval during the period from the start to the end of therapy with a fluoroscopic radiation photographing apparatus or the like installed integrally with a therapeutic radiation irradiation apparatus for example.

When an interval of fluoroscopic radiation photographing is reduced therefore, an interval of detecting the position of a target reduces and hence more accurate irradiation can be materialized. A problem of increasing the irradiation frequency of fluoroscopic radiation and increasing the use load of a fluoroscopic radiation photographing apparatus however arises.

The technologies of Japanese Unexamined Patent Application Publication (Translation of PCT Application) No. 2012-501792 and Japanese Unexamined Patent Application publication No. 2015-016161 stated earlier exist as technologies of changing the interval of fluoroscopic radiation photographing during medical treatment and improving the utilization efficiency of a fluoroscopic radiation photographing apparatus.

In Japanese Unexamined Patent Application Publication (Translation of PCT Application) No. 2012-501792, the movement of a target is measured during medical treatment and the interval of fluoroscopic radiation photographing is reduced when the movement of the target is larger than a specified value and the interval of fluoroscopic radiation photographing is expanded when the movement of the target is smaller than the specified value. By applying this method, the frequency of fluoroscopic radiation photographing can be reduced and the load of a fluoroscopic radiation photographing apparatus is expected to be reduced.

Further, in Japanese Unexamined Patent Application publication No. 2015-016161, when a diseased part projected over a fluoroscopic image of a test object photographed from a certain direction is not included in a designated region, fluoroscopic radiation photographing from another direction is refrained. By applying this method too, the frequency of fluoroscopic radiation photographing is reduced and the load of a fluoroscopic radiation photographing apparatus is expected to be reduced.

The following problems however exist in the above prior art.

That is, it has been clarified by the studies of the present inventors that the technology described in Japanese Unexamined Patent Application Publication (Translation of PCT Application) No. 2012-501792 stated above has the problem of: not being able to reduce an irradiation interval when the moving speed of a target is high; and not being able to reduce the load of a fluoroscopic radiation photographing apparatus. Further, it has also been clarified by the studies of the present inventors that, when the movement of a target in an irradiation permission region is not higher than a specified value, the frequency of measuring a target position lowers regardless of the inside and the outside of the irradiation permission region and hence the risk of not being able to sufficiently ensure the detection accuracy of the target and lowering the irradiation accuracy of therapeutic radiation arises.

Further, it has been clarified by the studies of the present inventors that the technology described in Japanese Unexamined Patent Application publication No. 2015-016161 stated above has the risk of falsely recognizing a structure as a target when the structure having a shape similar to the target (for example a blood vessel or the like) is projected over a fluoroscopic image because the fluoroscopic image is photographed only from one direction while the target projected over the fluoroscopic image is not included in a designated region. When such false recognition occurs, an operator has to: interrupt the irradiation of therapeutic radiation; and re-select a correct target while the fluoroscopic radiation is applied. It has been clarified by the studies of the present inventors that resultantly the problem of increasing treatment time and not necessarily being able to reduce the load of a fluoroscopic radiation photographing apparatus arises.

The present invention has been established in view of the above problems and an object of the present invention is to provide a radiation therapy system capable of not only inhibiting treatment time from increasing more effectively than before but also reducing the load of a fluoroscopic radiation photographing apparatus.

The present invention includes a plurality of means for solving the above problems and an example of the present invention is characterized by including: a therapeutic radiation irradiation apparatus to irradiate a target in a test object with therapeutic radiation; at least two fluoroscopic radiation photographing apparatuses to photograph a tracking object simultaneously from at least two directions by fluoroscopic radiation; a tracking object position computation apparatus to compute a three-dimensional position of the tracking object on the basis of images photographed by the fluoroscopic radiation photographing apparatuses; a therapeutic radiation irradiation control apparatus to judge whether or not the target exists in a predetermined irradiation permission region on the basis of the three-dimensional position of the tracking object computed by the tracking object position computation apparatus and control the therapeutic radiation irradiation apparatus so as to irradiate the target with the therapeutic radiation when the target is judged to exist in the irradiation permission region; and a fluoroscopic radiation photographing control apparatus to control irradiation quantities per unit time of the fluoroscopic radiation photographing apparatuses on the basis of the three-dimensional position of the tracking object.

The present invention makes it possible to not only inhibit treatment time from increasing more effectively than before but also reduce the loads of fluoroscopic radiation photographing apparatuses.

DETAILED DESCRIPTION

Embodiments of a radiation therapy system according to the present invention are explained hereunder in reference to the drawings.

Meanwhile, the following embodiments are explained on the basis of the case of using a charged particle beam such as a proton beam or a carbon beam as therapeutic radiation but X-rays, γ-rays, or the like can be used as therapeutic radiation.

First Embodiment

The first embodiment of a radiation therapy system according to the present invention is explained in reference to FIGS. 1 to 5.

Figure 1:
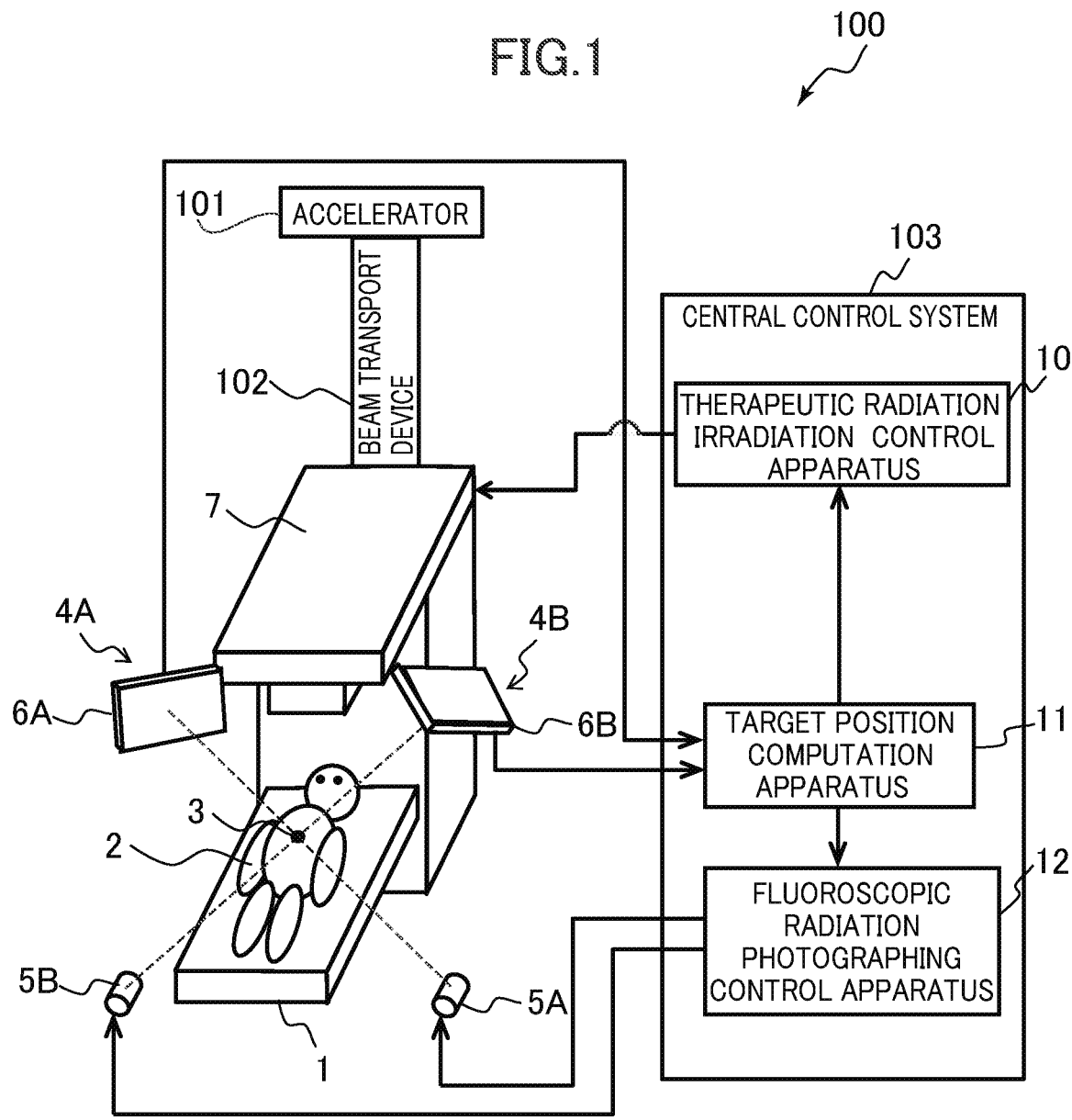
FIG. 1 is a schematic view showing a configuration of a radiation therapy system according to the first embodiment of the present invention.
Figure 2:
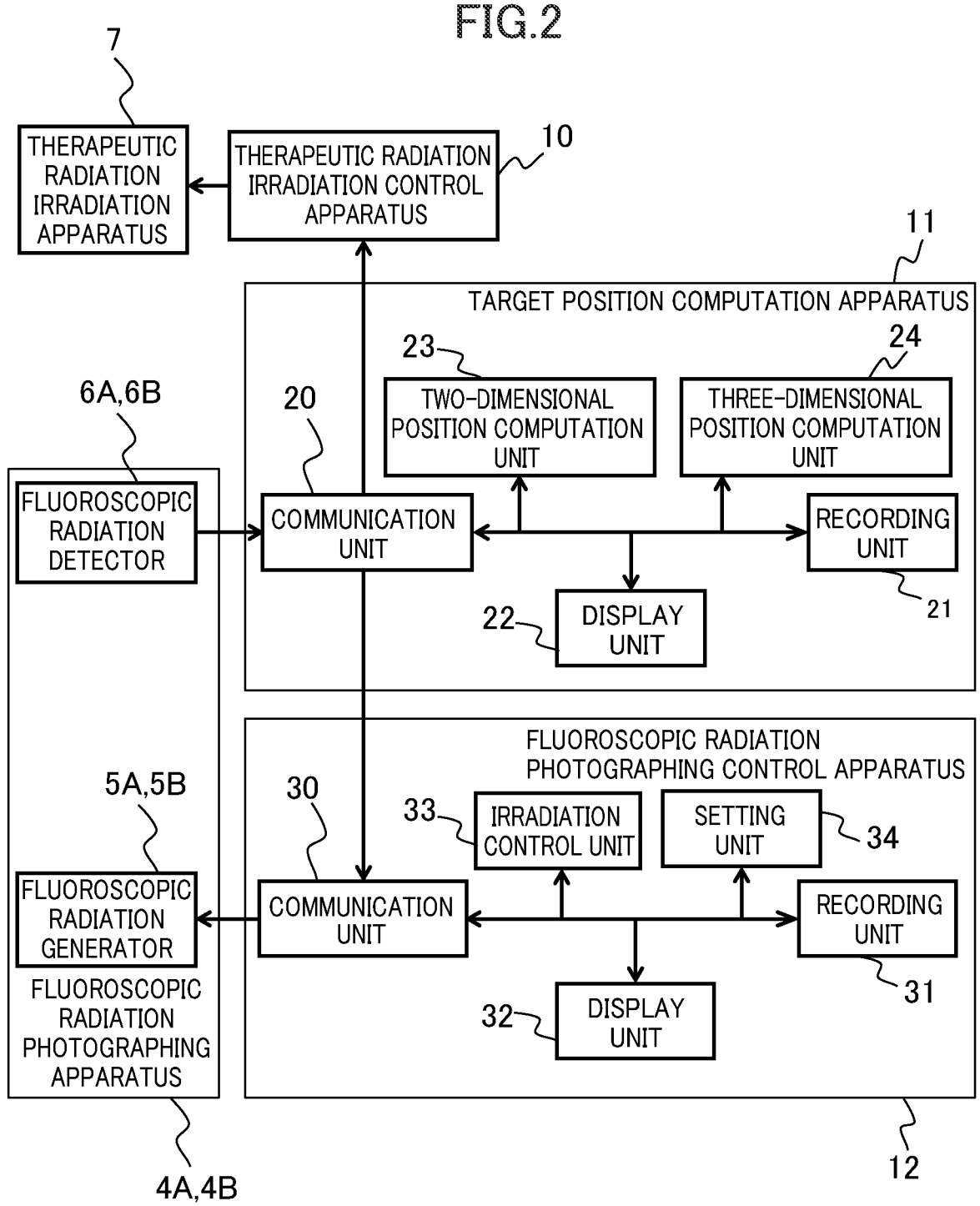
FIG. 2 is a block diagram showing functional configurations of a target position computation apparatus and a fluoroscopic radiation photographing control apparatus together with related apparatuses according to the first embodiment of the present invention.
Figure 3:
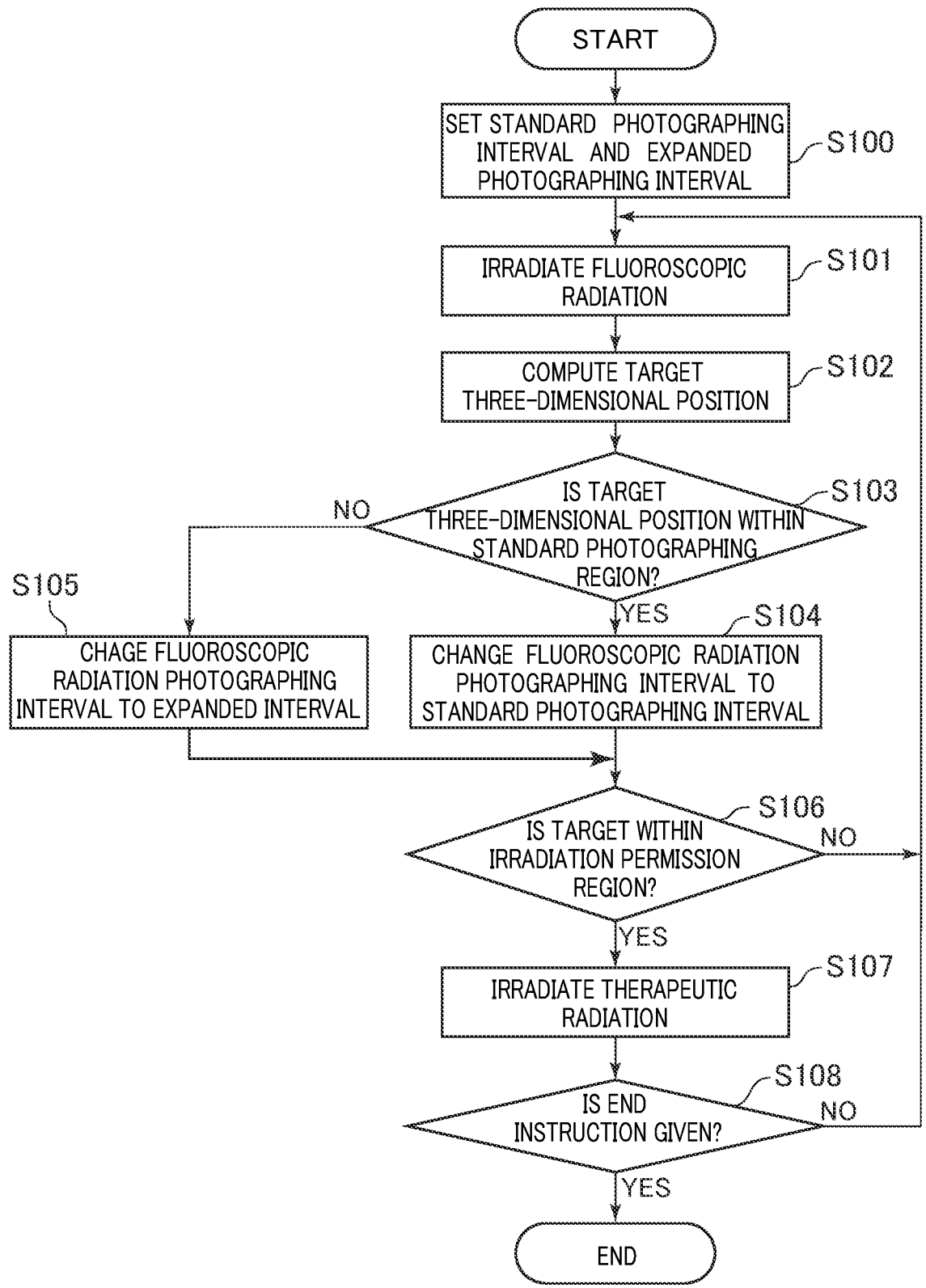
FIG. 3 is a view showing a processing flow of real-time image gated radiation therapy by a radiation therapy system according to the first embodiment of the present invention.

FIG. 1 is a view showing an overall schematic configuration of a radiation therapy system according to the present embodiment. FIG. 2 is a block diagram showing functional configurations of a target position computation apparatus and a fluoroscopic radiation photographing control apparatus together with related apparatuses according to the present embodiment. FIG. 3 is a view showing a processing flow of real-time image gated radiation therapy by a radiation therapy system according to the present embodiment.

In FIG. 1, a radiation therapy system 100 is an apparatus for irradiating a target 3 with a particle beam including heavy particles such as protons and carbon particles. The radiation therapy system 100 has an accelerator 101, a beam transport device 102, a treatment table 1 capable of positioning a test object 2, a therapeutic radiation irradiation apparatus 7 to irradiate the target 3 with a therapeutic particle beam supplied from the accelerator 101, fluoroscopic radiation photographing apparatuses 4A and 4B, a central control system 103, and others.

The therapeutic particle beam is accelerated to a necessary energy by the accelerator 101 installed in a room different from a treatment room and then introduced into the therapeutic radiation irradiation apparatus 7 through the beam transport device 102. The accelerator 101 can be a synchrotron type accelerator, a cyclotron type accelerator, or another accelerator.

Meanwhile, when X-rays are used as therapeutic radiation, an X-ray irradiation apparatus to generate therapeutic X-rays is installed in place of the accelerator 101 and the beam transport device 102. When γ-rays are used, a γ-ray irradiation apparatus to generate therapeutic γ-rays is installed in place of the accelerator 101 and the beam transport device 102.

The fluoroscopic radiation photographing apparatus 4A has: a fluoroscopic radiation generator 5A to generate fluoroscopic radiation toward the target 3 in the test object 2 from a first direction; a fluoroscopic radiation detector 6A to detect a two-dimensional dose distribution of fluoroscopic radiation that is generated from the fluoroscopic radiation generator 5A and transmitted through the test object 2; and a signal processing circuit (not shown in the figure).

The fluoroscopic radiation detector 6A outputs an analog signal from a detection element arranged two-dimensionally. The signal processing circuit: generates data of a fluoroscopic image by processing the analog signal from the fluoroscopic radiation detector 6A; and transmits the data to a target position computation apparatus 11.

Likewise, the fluoroscopic radiation photographing apparatus 4B has: a fluoroscopic radiation generator 5B to generate fluoroscopic radiation toward the test object 2 from a second direction different from the first direction; a fluoroscopic radiation detector 6B to detect a two-dimensional dose distribution of fluoroscopic radiation that is generated from the fluoroscopic radiation generator 5B and transmitted through the test object 2; and a signal processing circuit (not shown in the figure).

The fluoroscopic radiation detector 6B outputs an analog signal from a detection element arranged two-dimensionally. The signal processing circuit: generates data of a fluoroscopic image by processing the analog signal from the fluoroscopic radiation detector 6B; and transmits the data to the target position computation apparatus 11.

In the present embodiment, the photographing of the target 3 by the fluoroscopic radiation photographing apparatus 4B is carried out in synchronization with the photographing of the target 3 by the fluoroscopic radiation photographing apparatus 4A.

The target 3 is projected in each of the two fluoroscopic images obtained in synchronization with each other and the position of the target 3 is identified in each of the fluoroscopic images by template matching with a previously-prepared template image of the target 3. It takes a lot of search time to search the full range of a fluoroscopic image and hence it is desirable to search the position of the target 3 only within a range of a predetermined size around the position of the target 3 in the last fluoroscopic image.

The two lines of a line connecting the position of the target 3 detected by the template matching over the fluoroscopic radiation detector 6A with the fluoroscopic radiation generator 5A and a line connecting the position of the target 3 over the fluoroscopic radiation detector 6B with the fluoroscopic radiation generator 5B intersect with each other ideally at one point and the intersection point is regarded as the position where the target 3 exists.

Practically, however, because of the accuracy of template matching, the installation error of an X-ray fluoroscopic apparatus, and others, the two lines do not intersect with each other and are in the relationship of distortion in many cases. A perpendicular line common to each other can be drawn at the position where the two lines that are in the relationship of the distortion come closest to each other. The perpendicular line common to each other is referred to as a common perpendicular line. Then the midpoint of the common perpendicular line is regarded as the position of the target 3.

Meanwhile, when a target 3 is not detected correctly at least in one of the fluoroscopic images, for example when a structure resembling a target 3 is recognized as the target 3 through template matching in place of or in addition to the target 3 in one of the fluoroscopic images, an erroneous recognition line connecting the position of the structure over the fluoroscopic radiation detector 6A or 6B with the fluoroscopic radiation generator 5A or 5B is drawn. A common perpendicular line drawn between the erroneous recognition line and the other line comes to be longer than a common perpendicular line in a correctly recognized case. In the present embodiment therefore, a target 3 is traced accurately by using the principle of a common perpendicular line.

For example, in each of two fluoroscopic images, positions having matching scores higher than a predetermined value are listed up as candidates of the position of a target 3, the lengths of common perpendicular lines are computed for all the combinations from two candidate lists of the position of the target 3, and then the position of the target 3 is detected on the basis of the matching scores and the common perpendicular lines. On this occasion, it is possible to: weight the matching scores and the common perpendicular lines; select a most appropriate common perpendicular line on the basis of the result of the weighting; and detect the position of target 3.

Referring back to FIG. 1, the central control system 103: is a device to control the operations of various devices such as the accelerator 101, the beam transport device 102, the therapeutic radiation irradiation apparatus 7, the fluoroscopic radiation photographing apparatuses 4A and 4B, and others in the radiation therapy system 100; and has the target position computation apparatus 11, a therapeutic radiation irradiation control apparatus 10, a fluoroscopic radiation photographing control apparatus 12, and others.

The target position computation apparatus 11: is an apparatus to compute the position of a target 3 from images photographed by the fluoroscopic radiation photographing apparatuses 4A and 4B in real time; and has a communication unit 20, a recording unit 21, a display unit 22, a two-dimensional position computation unit 23, and a three-dimensional position computation unit 24 as shown in FIG. 2.

The communication unit 20 communicates with the fluoroscopic radiation photographing apparatuses 4A and 4B, the fluoroscopic radiation photographing control apparatus 12, the therapeutic radiation irradiation control apparatus 10, and others.

The recording unit 21 stores photographed images received from the fluoroscopic radiation photographing apparatuses 4A and 4B, computation results that will be described later, and others. In the recording unit 21, a projected image of a target 3 in the photographing direction of the fluoroscopic radiation photographing apparatus 4A is prepared beforehand and recorded as a first template image. Further, as a second template image, a projected image of a target 3 in the photographing direction of the fluoroscopic radiation photographing apparatus 4B is prepared beforehand and recorded.

The display unit 22 displays photographed images of the fluoroscopic radiation photographing apparatuses 4A and 4B, computation results that will be described later, and others.

The two-dimensional position computation unit 23 computes a two-dimensional position of a target 3 viewed from the photographing direction (first direction) of the fluoroscopic radiation photographing apparatus 4A by matching a photographed image of the fluoroscopic radiation photographing apparatus 4A and the first template image. Further, the two-dimensional position computation unit 23 computes a two-dimensional position of a target 3 viewed from the photographing direction (second direction) of the fluoroscopic radiation photographing apparatus 4B by matching a photographed image of the fluoroscopic radiation photographing apparatus 4B and the second template image. A computed two-dimensional position of a target 3 is associated with corresponding photographed images and stored in the recording unit 21.

The three-dimensional position computation unit 24 reversely projects two-dimensional positions of a target 3 viewed from the photographing directions of the fluoroscopic radiation photographing apparatuses 4A and 4B and computes a three-dimensional position of the target 3 also by using the aforementioned common perpendicular line from the computation results at the two-dimensional position computation unit 23. The computed three-dimensional position of the target 3 is recorded in the recording unit 21 and transmitted to the fluoroscopic radiation photographing control apparatus 12 and the therapeutic radiation irradiation control apparatus 10.

Further, the computed three-dimensional position of the target 3 is displayed over the display unit 22 together with the corresponding photographed images of the fluoroscopic radiation photographing apparatuses 4A and 4B. As a result, an operator can recognize the position of the target 3 in real time.

The fluoroscopic radiation photographing control apparatus 12: is a control apparatus to control the irradiation quantities per unit time of the fluoroscopic radiation generators 5A and 5B on the basis of a position of a target 3 measured by the target position computation apparatus 11; and has a communication unit 30, a recording unit 31, a display unit 32, an irradiation control unit 33, and a setting unit 34.

In particular, the fluoroscopic radiation photographing control apparatus 12 according to the present embodiment: judges whether or not a three-dimensional position of a target 3 is included in a standard photographing region at the irradiation control unit 33; and controls irradiation quantities per unit time by controlling photographing intervals of the fluoroscopic radiation photographing apparatuses so as to be expanded more when the three-dimensional position of the target 3 is not included in the standard photographing region than when the three-dimensional position of the target 3 is included in the standard photographing region.

The standard photographing region is decided on the basis of an irradiation permission region used for judging whether or not a therapeutic particle beam may be radiated in the therapeutic radiation irradiation control apparatus 10 that will be described later. For example, the standard photographing region can be an arbitrary region obtained by expanding an irradiation permission region by a predetermined quantity isotropically or anisotropically. Otherwise, the standard photographing region can be a region in a range exactly the same as an irradiation permission region or an arbitrary region obtained by contracting an irradiation permission region by a predetermined quantity.

The communication unit 30 communicates with the target position computation apparatus 11 and the fluoroscopic radiation generators 5A and 5B. The recording unit 31 stores a three-dimensional position of a target 3 received from the target position computation apparatus 11 and others. The display unit 32 displays judgment results that will be described later and others. The irradiation control unit 33 controls photographing intervals of fluoroscopic radiation by the fluoroscopic radiation generators 5A and 5B on the basis of a three-dimensional position of a target 3 stored in the recording unit 31. The setting unit 34 sets the fluoroscopic radiation generators 5A and 5B so that fluoroscopic radiation photographing intervals may be intervals controlled by the irradiation control unit 33.

The therapeutic radiation irradiation control apparatus 10: judges whether or not a three-dimensional position of a target 3 received from the target position computation apparatus 11 is included in a predetermined irradiation permission region; controls the therapeutic radiation irradiation apparatus 7 on the basis of the judgment results; and irradiates the target 3 with a therapeutic particle beam.

—Flow of Therapeutic Processing—

A processing flow of real-time image gated radiation therapy by the radiation therapy system 100 according to the present embodiment is explained in reference to FIG. 3.

Firstly, the fluoroscopic radiation photographing control apparatus 12 recognizes that an operator has set a standard photographing interval and an expanded photographing interval by using the setting unit 34 (Step S100).

The standard photographing interval at the present step: is a photographing interval of carrying out fluoroscopic radiation photographing when a three-dimensional position of a target 3 is included in a standard photographing region; and is set at a small value of the extent of being able to ensure the irradiation accuracy of a therapeutic particle beam. Otherwise, it is also possible to use a prefixed value as the standard photographing interval and the present step is excluded on this occasion.

Further, the expanded photographing interval: is a photographing interval of carrying out fluoroscopic radiation photographing when a three-dimensional position of a target 3 is not included in a standard photographing region; and is set at a value that is larger than a standard photographing interval but is small to the extent of being able to trace a target 3. Otherwise, it is possible to use a prefixed value also as the expanded photographing interval and the present step is excluded on this occasion.

Following Step S100, the irradiation control unit 33 transmits a fluoroscopic radiation irradiation signal to the fluoroscopic radiation generators 5A and 5B after a certain period of time has elapsed from a last fluoroscopic radiation irradiation time. The fluoroscopic radiation generators 5A and 5B that have received the fluoroscopic radiation irradiation signal generate fluoroscopic radiation toward the target 3 (Step S101). Here, the certain period of time is a time determined from the standard photographing interval or the expanded photographing interval that has been set at the preceding Step S100. Otherwise, it is possible to generate fluoroscopic radiation immediately after the start of the therapy without an interval of a certain period of time.

Following Step S101, fluoroscopic images generated by the fluoroscopic radiation photographing apparatuses 4A and 4B are transmitted to the target position computation apparatus 11 and a three-dimensional position of a target 3 is computed by the target position computation apparatus 11 (Step S102).

Following Step S102, the irradiation control unit 33 judges whether or not the three-dimensional position of the target 3 computed at Step S102 is included in the standard photographing region (Step S103).

When the judgment at Step S103 is "Yes" (the three-dimensional position of the target 3 is included in the standard photographing region), the irradiation control unit 33 in the fluoroscopic radiation photographing control apparatus 12 changes the photographing interval of the fluoroscopic radiation to the standard photographing interval (Step S104). In contrast, when the judgment at Step S103 is "No" (the three-dimensional position of the target 3 is not included in the standard photographing region), the irradiation control unit 33 changes the photographing interval of the fluoroscopic radiation to the expanded photographing interval (Step S105).

Following Step S104 or Step S105, the therapeutic radiation irradiation control apparatus 10 judges whether or not the three-dimensional position of the target 3 computed by the target position computation apparatus 11 is included in the irradiation permission region (Step S106).

When the judgment at Step S106 is "Yes" (the three-dimensional position of the target 3 is included in the irradiation permission region), the therapeutic radiation irradiation control apparatus 10 transmits a therapeutic particle beam irradiation signal to the therapeutic radiation irradiation apparatus 7 and irradiates the target 3 with a therapeutic particle beam (Step S107). In contrast, when the judgment at Step S106 is "No" (the three-dimensional position of the target 3 is not included in the irradiation permission region), the processing returns to Step S101.

Following Step S107, the therapeutic radiation irradiation control apparatus 10 and the fluoroscopic radiation photographing control apparatus 12 judge whether or not an end instruction (a specific instruction by an operator, an instruction of real-time image gating finish accompanying the end of therapeutic particle beam irradiation caused by the finish of irradiation designated by the therapeutic radiation irradiation apparatus 7, or another instruction) is given (Step S108).

When the judgment at Step S108 is "Yes" (an end instruction is given), the fluoroscopic radiation photographing and the irradiation of a therapeutic particle beam stop and real-time image gated radiation therapy finishes. In contrast, when the judgment at Step S108 is "No" (an end instruction is not given), the processing returns to Step S101 and the real-time image gated radiation therapy is continued.

—Effects—

Figure 4:
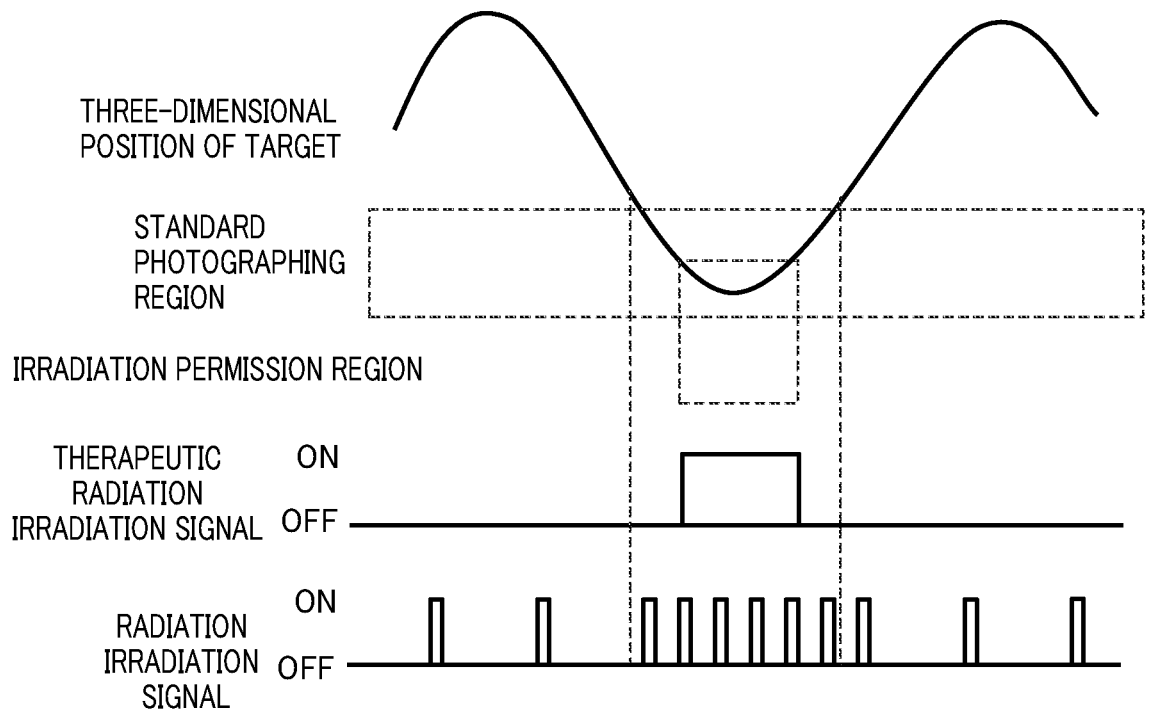
FIG. 4 is a timing chart showing the irradiation signals of a therapeutic particle beam and fluoroscopic radiation and the coordinates of a target according to the first embodiment of the present invention.
Figure 5:
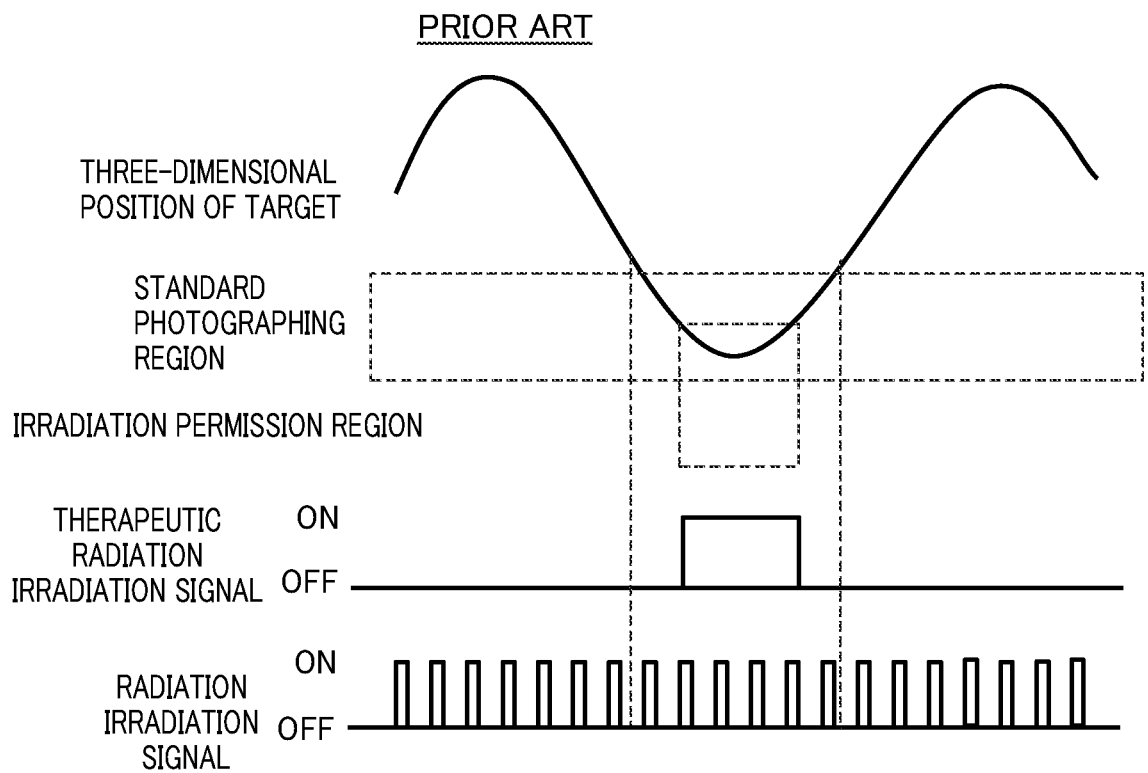
FIG. 5 is a timing chart showing the irradiation signals of a therapeutic particle beam and fluoroscopic radiation and the coordinates of a target in prior art.

The effects according to the present embodiment are explained in reference to FIGS. 4 and 5. FIG. 4 is a view showing an example of a timing chart of a therapeutic particle beam irradiation signal, fluoroscopic radiation irradiation signals, and three-dimensional positions of a target 3 when fluoroscopic radiation photographing control is carried out according to the present embodiment. FIG. 5 is a view showing an example of a timing chart of a therapeutic particle beam irradiation signal, fluoroscopic radiation irradiation signals, and three-dimensional positions of a target 3 in a conventional case.

Here, although a position of a target 3 should be represented by a three-dimensional position in nature, in FIGS. 4 and 5, a three-dimensional position of a target 3 is regarded as varying cyclically only in a certain direction in order to simplifying the explanations.

In FIGS. 4 and 5, the therapeutic radiation irradiation apparatus 7 irradiates a target 3 with a therapeutic particle beam while the therapeutic particle beam irradiation signal is in the state of ON. Likewise, the fluoroscopic radiation generators 5A and 5B generate fluoroscopic radiation toward the target 3 while the fluoroscopic radiation irradiation signals are in the state of ON.

As shown in FIG. 4, in the fluoroscopic radiation photographing control according to the present embodiment, the intervals at which the fluoroscopic radiation irradiation signals are in the state of ON expand more when a three-dimensional position of a target 3 is not included in a standard photographing region than when a three-dimensional position of the target 3 is included in the standard photographing region. As a result, the frequency at which the fluoroscopic radiation irradiation signals are in the state of ON reduces and the frequency at which the fluoroscopic radiation generators 5A and 5B emit fluoroscopic radiation reduces in comparison with conventional control shown in FIG. 5.

Meanwhile, with regard to the timing at which the therapeutic particle beam irradiation signal is in the state of ON, there is no difference between the fluoroscopic radiation photographing control according to the present embodiment shown in FIG. 4 and the conventional fluoroscopic radiation photographing control shown in FIG. 5.

As stated above, according to the present embodiment, since the frequency at which the fluoroscopic radiation generators 5A and 5B generate fluoroscopic radiation can be reduced without changing the timing of emitting a therapeutic particle beam, it is possible to reduce the loads of the fluoroscopic radiation generators 5A and 5B while the accuracy of irradiating a target 3 with the therapeutic particle beam is maintained. Further, it is possible to trace a target 3 with a high degree of accuracy even when photographing conditions are severe by synchronizing the photographing of fluoroscopic radiation from two directions. In other words, it is possible to: reduce the frequency of losing sight of a target 3 in comparison with a conventional case; and avoid the operator's labor of redetecting the target 3 during losing sight of the target 3. As a result, irradiation time can be shortened. Further, it is possible to: reduce the frequency of photographing by fluoroscopic radiation by shortening irradiation time; and attempt to further reduce the loads of the fluoroscopic radiation photographing apparatuses.

Second Embodiment

Figure 6:
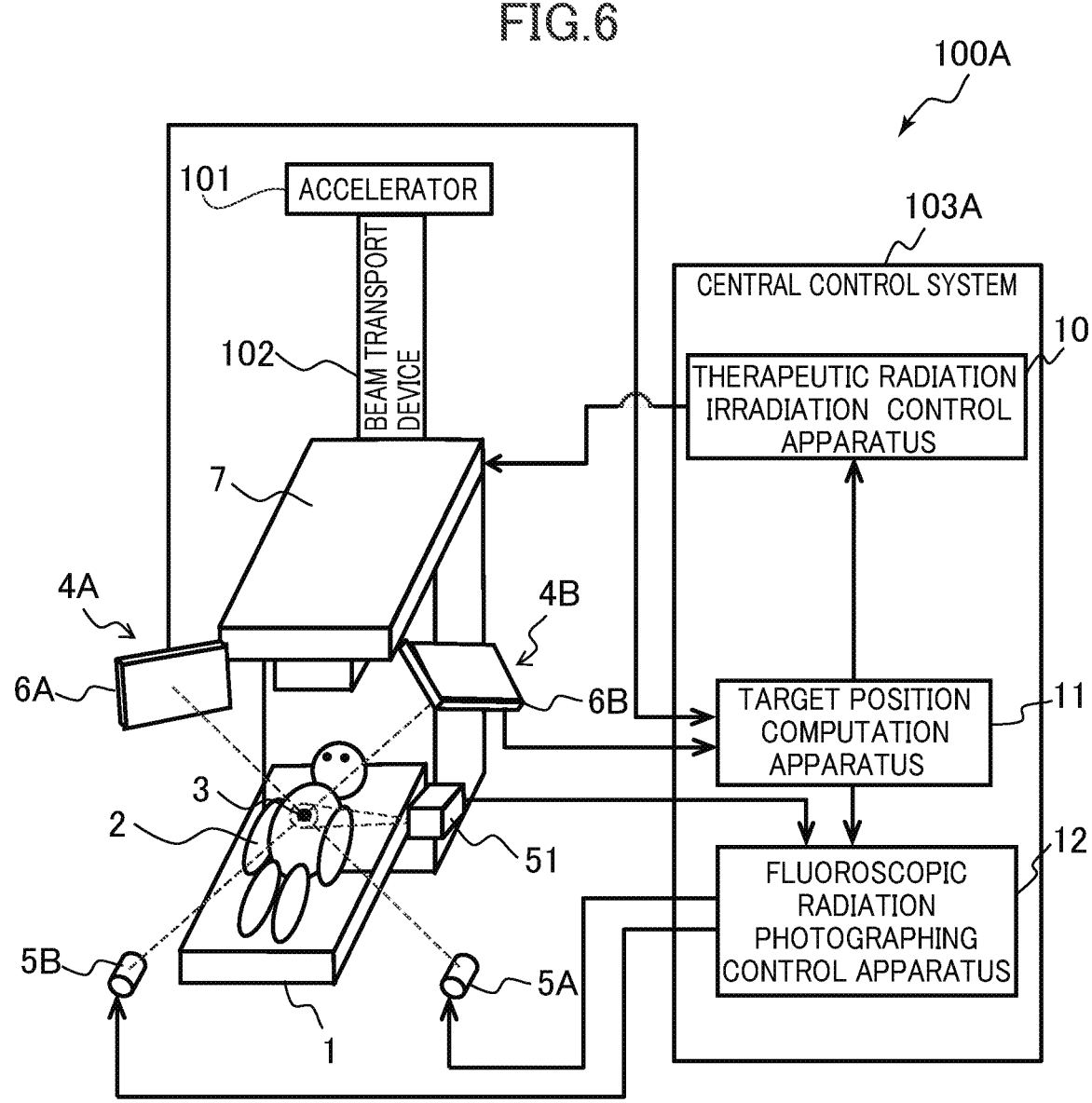
FIG. 6 is a schematic view showing a configuration of a radiation therapy system according to the second embodiment of the present invention.
Figure 7:
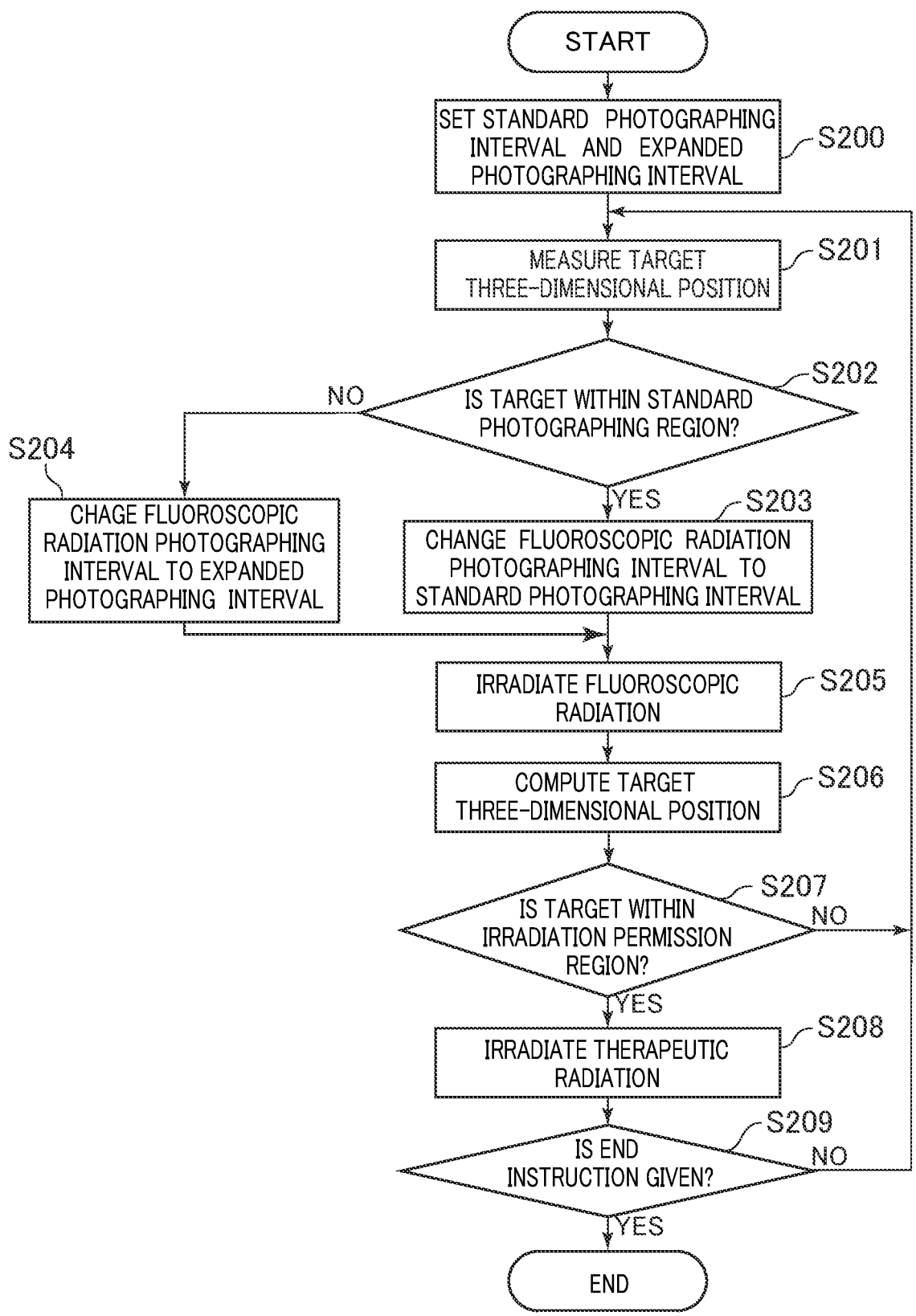
FIG. 7 is a view showing a processing flow of real-time image gated radiation therapy by a radiation therapy system according to the second embodiment of the present invention.

A radiation therapy system according to the second embodiment of the present invention is explained in reference to FIGS. 6 and 7. FIG. 6 is a schematic view showing a configuration of a radiation therapy system according to the present embodiment. FIG. 7 is a view showing a processing flow of real-time image gated radiation therapy by a radiation therapy system according to the present embodiment.

As shown in FIG. 6, a radiation therapy system 100A according to the present embodiment measures a three-dimensional position of a target 3 with an external sensor 51. Here, a part in the radiation therapy system 100A according to the present embodiment identical to a part in the radiation therapy system 100 according to the first embodiment stated earlier is represented by an identical reference sign and the explanations are omitted appropriately.

In FIG. 6, the radiation therapy system 100A according to the present embodiment has an external sensor 51 in addition to an accelerator 101, a beam transport device 102, a treatment table 1, a therapeutic radiation irradiation apparatus 7, fluoroscopic radiation photographing apparatuses 4A and 4B, and a central control system 103A.

The external sensor 51: measures a three-dimensional position of a target 3 intermittently from the exterior of a test object 2; and transmits the three-dimensional positional data of the target 3 to a fluoroscopic radiation photographing control apparatus 12A. As the external sensor 51 cited here, an ultrasonic sensor, an MRI, or the like is named. For example, when the target 3 is a prostate, the three-dimensional position of the target 3 can be measured by using an ultrasonic sensor. Likewise, the three-dimensional position of the target 3 can be measured also by using an MRI.

The central control system 103A includes a target position computation apparatus 11, a therapeutic radiation irradiation control apparatus 10, and the fluoroscopic radiation photographing control apparatus 12A.

The fluoroscopic radiation photographing control apparatus 12A: receives a three-dimensional position of a target 3 from the external sensor 51 through a communication unit 30; and controls irradiation intervals of fluoroscopic radiation generated by fluoroscopic radiation generators 5A and 5B on the basis of the received three-dimensional position of the target 3.

Other configurations and operations are nearly the same as the configurations and operations of the apparatuses in the radiation therapy system 100 according to the first embodiment stated earlier and the details are omitted.

—Flow of Therapeutic Processing—

A processing flow of real-time image gated radiation therapy by the radiation therapy system according to the present embodiment is explained in reference to FIG. 7.

Firstly, the fluoroscopic radiation photographing control apparatus 12A recognizes that an operator has set a standard photographing interval and an expanded photographing interval by using a setting unit 34 (Step S200).

The standard photographing interval and the expanded photographing interval at the present step can be nearly the same as those at Step S100 in the first embodiment. Further, in the present embodiment, it is possible to set an infinitely large value as the expanded photographing interval. When an infinitely large value is set as the expanded photographing interval, fluoroscopic radiation is not applied while a three-dimensional position of a target 3 is not included in a standard photographing region. By such control, the loads of the fluoroscopic radiation photographing apparatuses 4A and 4B can be attempted to be reduced further.

Following Step S200, a three-dimensional position of a target 3 in a test object 2 is measured by the external sensor 51 (Step S201).

Following Step S201, the fluoroscopic radiation photographing control apparatus 12A judges whether or not the three-dimensional position of the target 3 measured by the external sensor 51 at Step S201 is included in the standard photographing region (Step S202).

When the judgment at Step S202 is "Yes" (the three-dimensional position of the target 3 is included in the standard photographing region), the fluoroscopic radiation photographing control apparatus 12A changes the photographing interval of the fluoroscopic radiation to the standard photographing interval (Step S203). In contrast, when the judgment at Step S202 is "No" (the three-dimensional position of the target 3 is not included in the standard photographing region), the fluoroscopic radiation photographing control apparatus 12A changes the photographing interval of the fluoroscopic radiation to the expanded photographing interval (Step S204).

Following Step S203 or Step S204, the fluoroscopic radiation photographing control apparatus 12A transmits fluoroscopic radiation irradiation signals to the fluoroscopic radiation generators 5A and 5B after a certain period of time has elapsed from a last fluoroscopic radiation irradiation time. The fluoroscopic radiation generators 5A and 5B that have received the fluoroscopic radiation irradiation signals generate fluoroscopic radiation toward the target 3 (Step S205).

Following Step S205, fluoroscopic images generated by the fluoroscopic radiation photographing apparatuses 4A and 4B are transmitted to the target position computation apparatus 11 and the three-dimensional position of the target 3 is computed (Step S206).

Following Step S206, the therapeutic radiation irradiation control apparatus 10 judges whether or not the three-dimensional position of the target 3 computed by the target position computation apparatus 11 is included in an irradiation permission region (Step S207).

When the judgment at Step S207 is "Yes" (the three-dimensional position of the target 3 is included in the irradiation permission region), the therapeutic radiation irradiation control apparatus 10 transmits a therapeutic particle beam irradiation signal to the therapeutic radiation irradiation apparatus 7 and irradiates the target 3 with a therapeutic particle beam (Step S208). In contrast, when the judgment at Step S207 is "No" (the three-dimensional position of the target 3 is not included in the irradiation permission region), the processing returns to Step S201.

Following Step S208, the therapeutic radiation irradiation control apparatus 10 and the fluoroscopic radiation photographing control apparatus 12A judge whether or not an end instruction (a specific instruction by an operator, an instruction of real-time image gating finish accompanying the end of therapeutic particle beam irradiation caused by the finish of irradiation designated by the therapeutic radiation irradiation apparatus 7, or another instruction) is given (Step S209).

When the judgment at Step S209 is "Yes" (an end instruction is given), the fluoroscopic radiation photographing and the irradiation of a therapeutic particle beam stop and real-time image gated radiation therapy finishes. In contrast, when the judgment at Step S209 is "No" (an end instruction is not given), the processing returns to Step S201 and the real-time image gated radiation therapy is continued.

—Effects—

In the radiation therapy system 100A according to the present embodiment too, effects nearly similar to the effects of the radiation therapy system 100 according to the first embodiment stated earlier are obtained.

Further, in the present embodiment, since a three-dimensional position of a target 3 is measured by the external sensor 51, it is possible to: set the expanded photographing interval at a value larger than the first embodiment or an infinitely large value; and further reduce the loads of the fluoroscopic radiation generators 5A and 5B.

Third Embodiment

Figure 8:
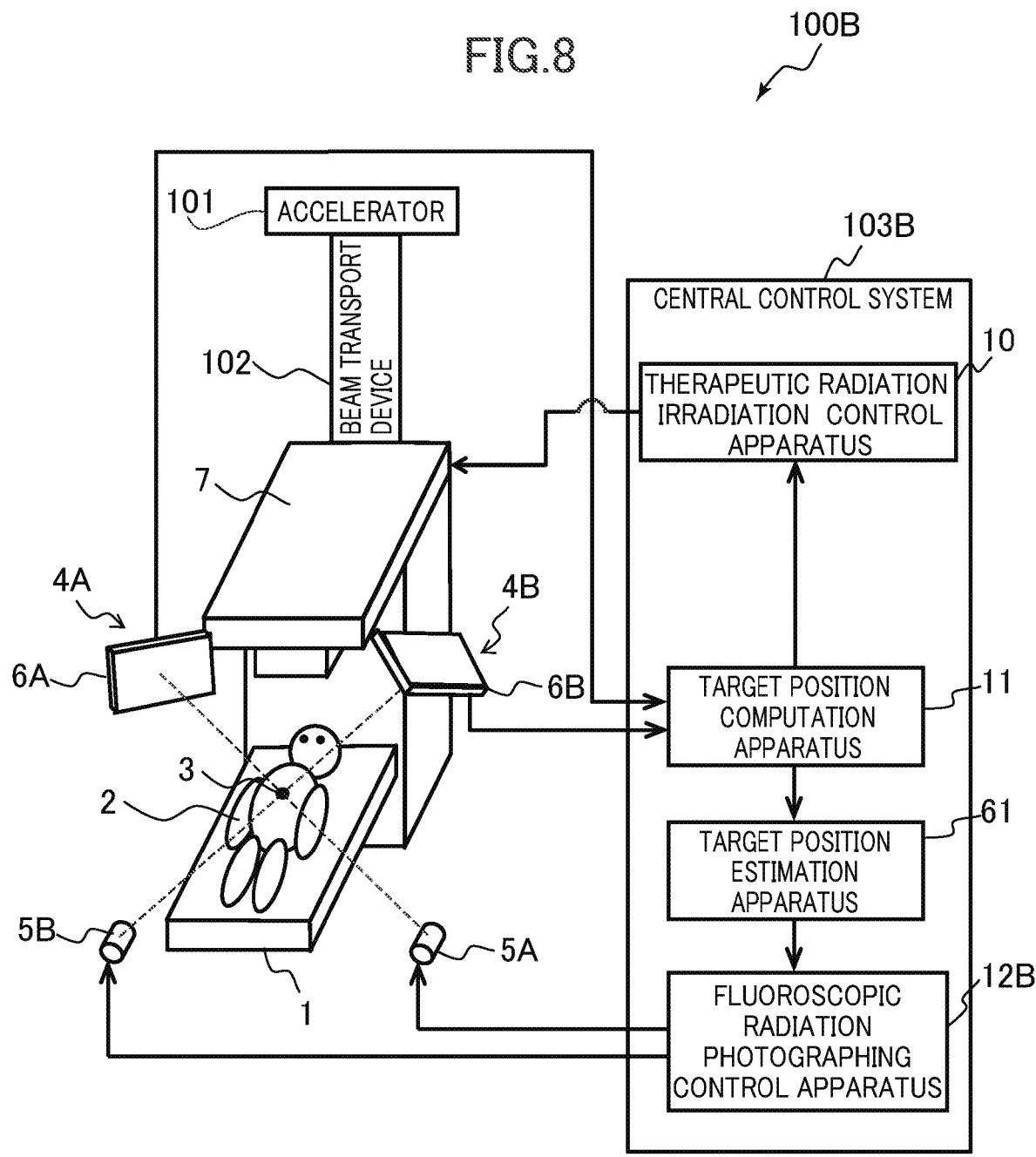
FIG. 8 is a schematic view showing a configuration of a radiation therapy system according to the third embodiment of the present invention.
Figure 9:
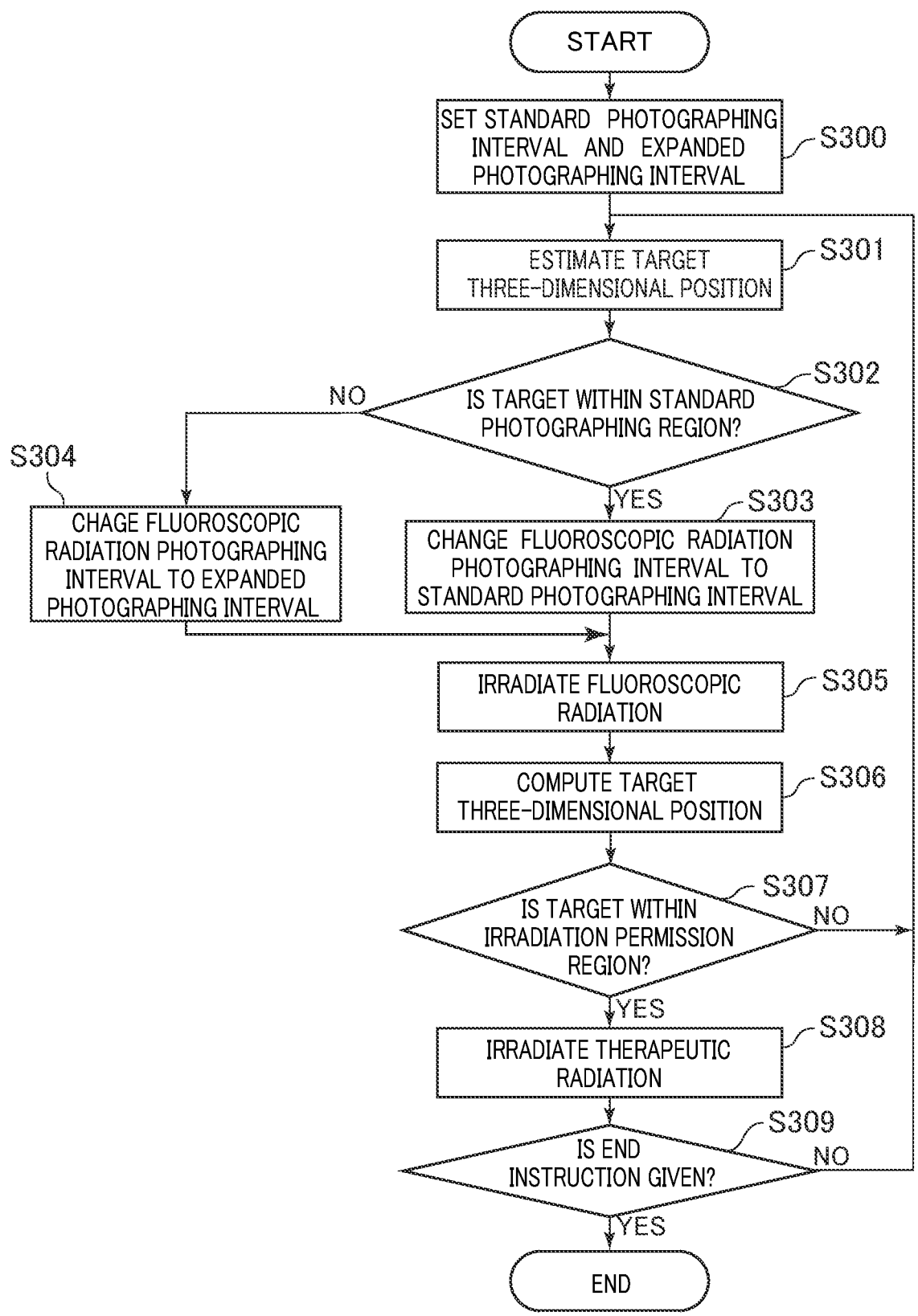
FIG. 9 is a view showing a processing flow of real-time image gated radiation therapy by a radiation therapy system according to the third embodiment of the present invention.

A radiation therapy system according to the third embodiment of the present invention is explained in reference to FIGS. 8 and 9. FIG. 8 is a schematic view showing a configuration of a radiation therapy system according to the present embodiment. FIG. 9 is a view showing a processing flow of real-time image gated radiation therapy by a radiation therapy system according to the present embodiment.

A radiation therapy system 100B according to the present embodiment estimates a three-dimensional position of a target 3 and judges whether or not the estimated three-dimensional position is included in a predetermined region.

In FIG. 8, the radiation therapy system 100B according to the present embodiment has an accelerator 101, a beam transport device 102, a treatment table 1, a therapeutic radiation irradiation apparatus 7, fluoroscopic radiation photographing apparatuses 4A and 4B, and a central control system 103B.

The central control system 103B includes a target position estimation apparatus 61 to estimate a three-dimensional position of a target 3 in addition to a target position computation apparatus 11, a therapeutic radiation irradiation control apparatus 10, and a fluoroscopic radiation photographing control apparatus 12B.

The target position estimation apparatus 61: records three-dimensional positional data of a target 3 computed by the target position computation apparatus 11 in chronological order; and estimates the present three-dimensional position of the target 3 on the basis of the recorded three-dimensional positional data. Here, various arbitrary methods can be used for estimating a three-dimensional position of a target 3. For example, when the variation of a three-dimensional position of a target 3 is assumed to be the same as the respiratory cycle of a test object 2, the three-dimensional position of the target 3 can be estimated from a present respiratory phase. Here, three-dimensional positional data of a target 3 obtained before the start of medical treatment may also be used as three-dimensional positional data of a target 3 recorded by the target position estimation apparatus 61.

The fluoroscopic radiation photographing control apparatus 12B: receives a three-dimensional position of a target 3 estimated by the target position estimation apparatus 61 through a communication unit 30; and controls the irradiation intervals of fluoroscopic radiation of fluoroscopic radiation generators 5A and 5B on the basis of the received three-dimensional position of the target 3.

Other configurations and operations are nearly the same as the configurations and operations of the apparatuses in the radiation therapy system 100 according to the first embodiment stated earlier and the details are omitted.

—Flow of Therapeutic Processing—

A processing flow of real-time image gated radiation therapy by the radiation therapy system according to the present embodiment is explained in reference to FIG. 9.

Firstly, the fluoroscopic radiation photographing control apparatus 12B recognizes that an operator has set a standard photographing interval and an expanded photographing interval by using a setting unit 34 (Step S300). The standard photographing interval is nearly the same as that at Step S100 in the first embodiment. The expanded photographing interval at the present step: is a photographing interval of fluoroscopic radiation photographing when a three-dimensional position of a target 3 is not included in a standard photographing region; and is set at a value larger than the standard photographing interval. Otherwise, a prefixed value can be used also as an expanded photographing interval and the present step is excluded on this occasion.

Following Step S300, the target position estimation apparatus 61 estimates a present three-dimensional position of the target 3 on the basis of the recorded three-dimensional positional data of the target 3 (Step S301).

Following Step S301, the fluoroscopic radiation photographing control apparatus 12B judges whether or not the three-dimensional position of the target 3 estimated by the target position estimation apparatus 61 at Step S301 is included in the standard photographing region (Step S302).

When the judgment at Step S302 is "Yes" (the estimated three-dimensional position of the target 3 is included in the standard photographing region), the fluoroscopic radiation photographing control apparatus 12B changes the photographing interval of the fluoroscopic radiation to the standard photographing interval (Step S303). In contrast, when the judgment at Step S302 is "No" (the estimated three-dimensional position of the target 3 is not included in the standard photographing region), the fluoroscopic radiation photographing control apparatus 12B changes the photographing interval of the fluoroscopic radiation to the expanded photographing interval (Step S304).

Following Step S303 or Step S304, the fluoroscopic radiation photographing control apparatus 12B transmits fluoroscopic radiation irradiation signals to the fluoroscopic radiation generators 5A and 5B after a certain period of time has elapsed from a last fluoroscopic radiation irradiation time. The fluoroscopic radiation generators 5A and 5B that have received the fluoroscopic radiation irradiation signals generate fluoroscopic radiation toward the target 3 (Step S305).

Following Step S305, fluoroscopic images generated by the fluoroscopic radiation photographing apparatuses 4A and 4B are transmitted to the target position computation apparatus 11 and the three-dimensional position of the target 3 is computed (Step S306).

Following Step S306, the therapeutic radiation irradiation control apparatus 10 judges whether or not the three-dimensional position of the target 3 computed by the target position computation apparatus 11 is included in an irradiation permission region (Step S307).

When the judgment at Step S307 is "Yes" (the three-dimensional position of the target 3 is included in the irradiation permission region), the therapeutic radiation irradiation control apparatus 10 transmits a therapeutic particle beam irradiation signal to the therapeutic radiation irradiation apparatus 7 and irradiates the target 3 with a therapeutic particle beam (Step S308). In contrast, when the judgment at Step S307 is "No" (the computed three-dimensional position of the target 3 is not included in the irradiation permission region), the processing returns to Step S301.

Following Step S308, the therapeutic radiation irradiation control apparatus 10 and the fluoroscopic radiation photographing control apparatus 12B judge whether or not an end instruction (a specific instruction by an operator, an instruction of real-time image gating finish accompanying the end of therapeutic particle beam irradiation caused by the finish of irradiation designated by the therapeutic radiation irradiation apparatus 7, or another instruction) is given (Step S309).

When the judgment at Step S309 is "Yes" (an end instruction is given), the fluoroscopic radiation photographing and the irradiation of a therapeutic particle beam stop and real-time image gated radiation therapy finishes. In contrast, when the judgment at Step S309 is "No" (an end instruction is not given), the processing returns to Step S301 and the real-time image gated radiation therapy is continued.

—Effects—

In the radiation therapy system 100B according to the present embodiment too, effects nearly similar to the effects of the radiation therapy system 100 according to the first embodiment stated earlier are obtained.

Further, in the present embodiment, since the target position estimation apparatus 61 to estimate a three-dimensional position of a target 3 is further arranged, it is possible to obtain a three-dimensional position of a target 3 even when fluoroscopic radiation is not applied. It is therefore possible to: set a standard photographing interval and an expanded photographing interval at values larger than those in the first embodiment; and further reduce the loads of the fluoroscopic radiation generators 5A and 5B.

Fourth Embodiment

Figure 10:
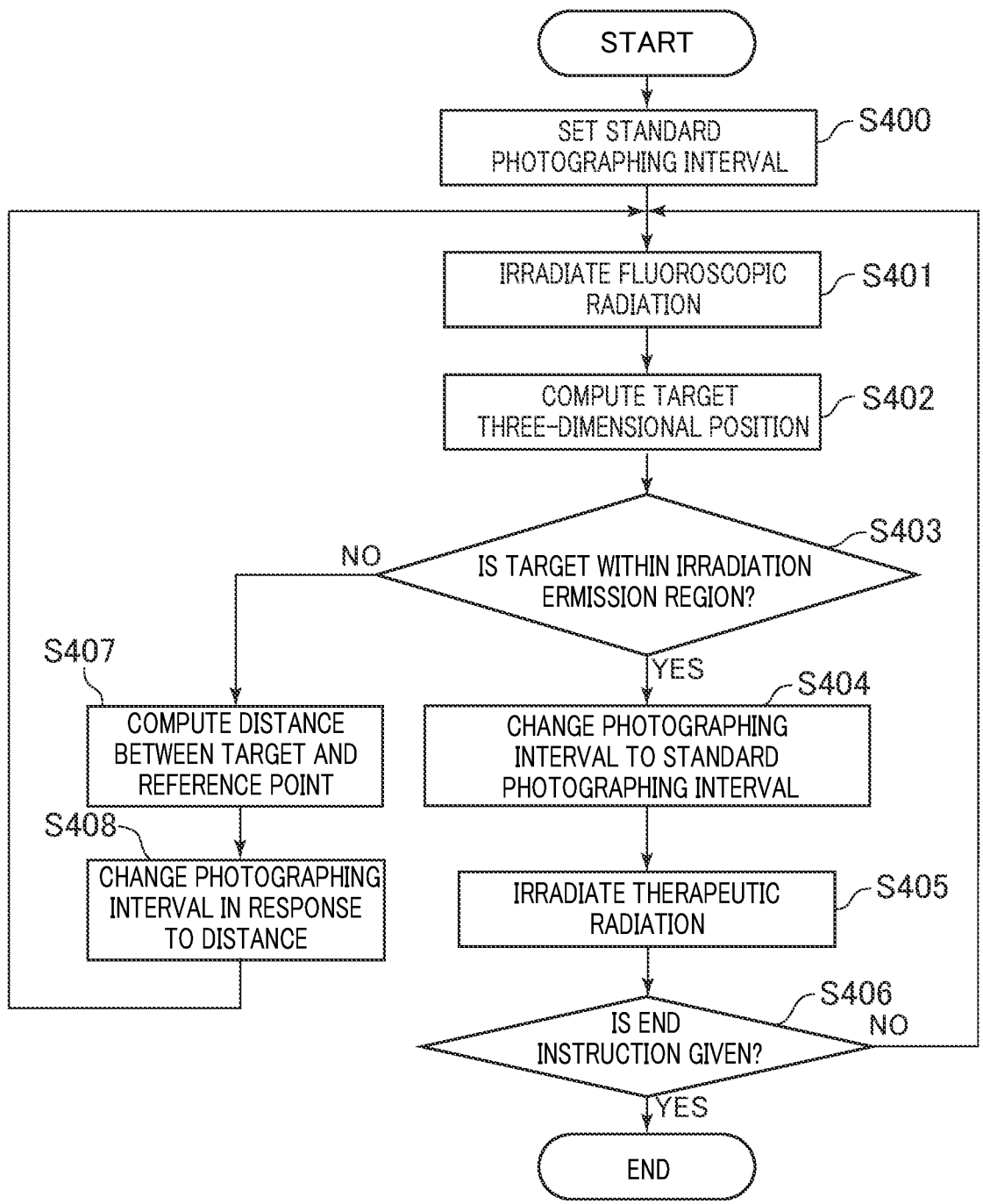
FIG. 10 is a view showing a processing flow of real-time image gated radiation therapy by a radiation therapy system according to the fourth embodiment of the present invention.

A radiation therapy system according to the fourth embodiment of the present invention is explained in reference to FIG. 10. FIG. 10 is a view showing a processing flow of real-time image gated radiation therapy by a radiation therapy system according to the present embodiment.

A radiation therapy system according to the fourth embodiment of the present invention is explained. The radiation therapy system according to the present embodiment has a configuration nearly identical to any one of the radiation therapy systems 100, 100A, and 100B according to the first to third embodiments.

The difference is to control irradiation quantities per unit time of fluoroscopic radiation generators 5A and 5B on the basis of a distance between a three-dimensional position of a target 3 and a reference point in a fluoroscopic radiation photographing control apparatus 12, 12A, or 12B. Here, the reference point is decided on the basis of an irradiation permission region. For example, the reference point can be the center of gravity of an irradiation permission region or an arbitrary point obtained by contracting an irradiation permission region isotropically or anisotropically.

Other configurations and operations are nearly the same as the configurations and operations of the apparatuses in the radiation therapy system 100 according to the first embodiment, the radiation therapy system 100A according to the second embodiment, and the radiation therapy system 100B according to the third embodiment, those being stated earlier, and the details are omitted.

—Flow of Therapeutic Processing—

A processing flow of real-time image gated radiation therapy by the radiation therapy system according to the present embodiment when the present embodiment is based on the first embodiment is explained in reference to FIG. 10.

Firstly, the fluoroscopic radiation photographing control apparatus 12, 12A or 12B recognizes that an operator has set a standard photographing interval and an expanded photographing interval by using a setting unit 34 (Step S400).

The standard photographing interval at the present step: is a photographing interval of fluoroscopic radiation when a three-dimensional position of a target 3 is included in an irradiation permission region; and is set at a small value of the extent of being able to ensure the irradiation accuracy of a therapeutic particle beam. Otherwise, a prefixed value can be used as a standard photographing interval and the present step is excluded on this occasion.

Following Step S400, the fluoroscopic radiation photographing control apparatus 12, 12A or 12B controls the fluoroscopic radiation generators 5A and 5B and generates fluoroscopic radiation toward the target 3 (Step S401).

Following Step S401, fluoroscopic images generated by fluoroscopic radiation photographing apparatuses 4A and 4B are transmitted to a target position computation apparatus 11 and a three-dimensional position of the target 3 is computed (Step S402).

Following Step S402, a therapeutic radiation irradiation control apparatus 10 judges whether or not the three-dimensional position of the target 3 computed by the target position computation apparatus 11 is included in the irradiation permission region (Step S403).

When the judgment at Step S403 is "Yes" (the three-dimensional position of the target 3 is included in the irradiation permission region), the therapeutic radiation irradiation control apparatus 10 outputs a change signal to the fluoroscopic radiation photographing control apparatus 12, 12A, or 12B so as to change the photographing interval of fluoroscopic radiation to the standard photographing interval and the fluoroscopic radiation photographing control apparatus 12, 12A, or 12B changes the photographing interval (Step S404).

Following Step S404, the therapeutic radiation irradiation control apparatus 10 transmits a therapeutic particle beam irradiation signal to a therapeutic radiation irradiation apparatus 7 and irradiates the target 3 with a therapeutic particle beam (Step S405).

Following Step S405, the therapeutic radiation irradiation control apparatus 10 judges whether or not an end instruction (a specific instruction by an operator, an instruction of real-time image gating finish accompanying the end of therapeutic particle beam irradiation caused by the finish of irradiation designated by the therapeutic radiation irradiation apparatus 7, or another instruction) is given (Step S406).

When the judgment at Step S406 is "Yes" (an end instruction is given), the therapeutic radiation irradiation control apparatus 10: outputs a fluoroscopy end signal to the fluoroscopic radiation photographing control apparatus 12, 12A, or 12B; stops fluoroscopic radiation photographing and the irradiation of the therapeutic particle beam; and finishes real-time image gated radiation therapy. In contrast, when the judgment at Step S406 is "No" (an end instruction is not given), the processing returns to Step S401 and the real-time image gated radiation therapy is continued.

On the other hand, when the judgment at Step S403 is "No" (the three-dimensional position of the target 3 is not included in the irradiation permission region), the therapeutic radiation irradiation control apparatus 10 outputs a change signal to the fluoroscopic radiation photographing control apparatus 12, 12A, or 12B so as to change the photographing interval of fluoroscopic radiation. The fluoroscopic radiation photographing control apparatus 12, 12A, or 12B: receives the three-dimensional positional data of the target 3 from the target position computation apparatus 11 by receiving the input of the change signal; and computes a distance between the target 3 and the reference point (Step S407).

Following Step S407, the fluoroscopic radiation photographing control apparatus 12, 12A, or 12B changes a photographing interval of photographing fluoroscopic radiation in response to a distance computed at Step S407 (Step S408).

The change of the photographing interval at the present step means to: expand the photographing interval when the distance from a reference point to a three-dimensional position of a target 3 is large; and reduce the photographing interval but so as to be a value larger than the standard photographing interval when the distance from the reference point to the three-dimensional position of a target 3 is small. After changing the photographing interval, the processing returns to Step S401.

—Effects—

In the radiation therapy system according to the present embodiment too, effects nearly similar to the effects of the radiation therapy system 100 according to the first embodiment, the radiation therapy system 100A according to the second embodiment, and the radiation therapy system 100B according to the third embodiment, those being stated earlier, are obtained.

Further, in the present embodiment, the fluoroscopic radiation photographing control apparatus 12, 12A, or 12B: can expand a photographing interval when a three-dimensional position of a target 3 separates from the reference point by controlling irradiation quantities per unit time of the fluoroscopic radiation photographing apparatuses 4A and 4B on the basis of the distance between the three-dimensional position of the target 3 and the reference point; can change the photographing frequencies of the fluoroscopic radiation generators 5A and 5B continuously; and hence can reduce the loads of the fluoroscopic radiation photographing apparatuses 4A and 4B more effectively.

Other Modifications

Meanwhile, the present invention is not limited to the aforementioned embodiments and can consider various modifications. For example, the aforementioned embodiments are explained in detail in order to make the present invention easy to understand and are not necessarily limited to the embodiments having all the explained configurations. Further, a part of the configuration of each of the embodiments can be added to, deleted from, or replaced with a part of the configuration of another embodiment.

For example, the present invention can take the features of the following modifications.

First Modification

Figure 11:
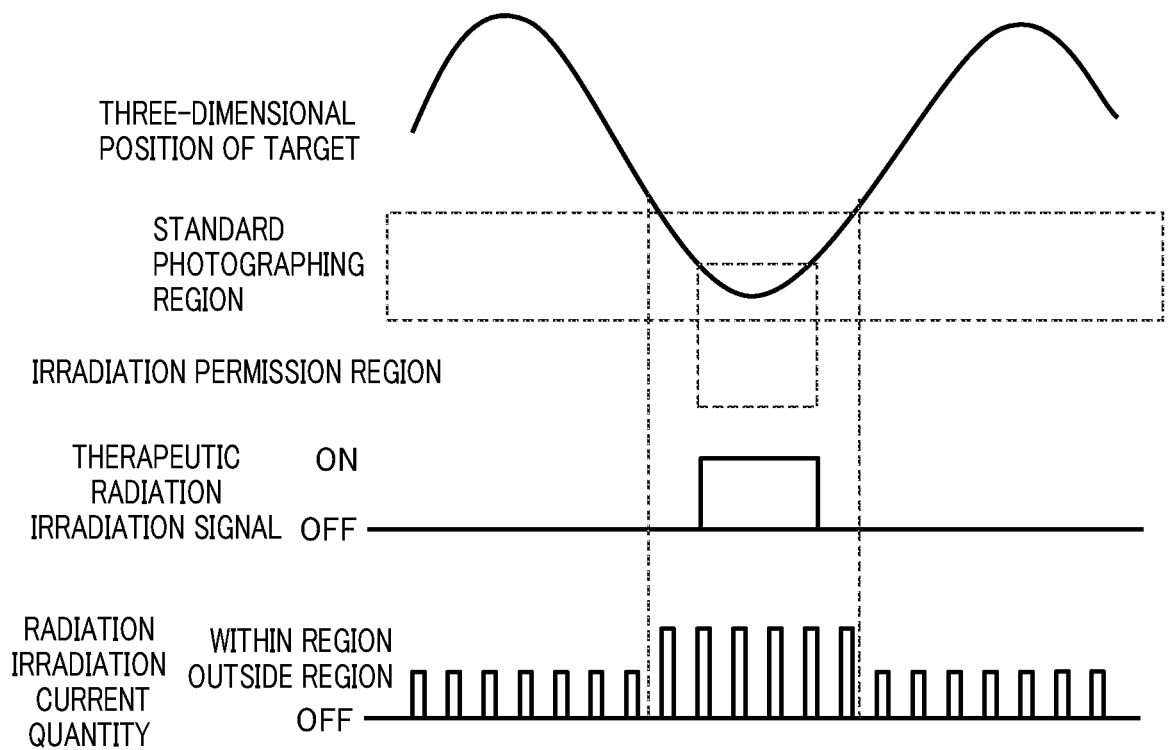
FIG. 11 is a timing chart showing the irradiation signals of a therapeutic particle beam and fluoroscopic radiation and the coordinates of a target according to the first modification of the present invention.

As a modification of the first to fourth embodiments, the quantities of electric current supplied to fluoroscopic radiation generators 5A and 5B can be changed as shown in FIG. 11 in place of adjusting the irradiation intervals of fluoroscopic radiation by the fluoroscopic radiation generators 5A and 5B. FIG. 11 is a timing chart showing the irradiation signals of a therapeutic particle beam and fluoroscopic radiation and the coordinates of a target according to the present first modification.

A step of setting a standard current quantity and a reduced current quantity is carried out in place of Step S100 shown in FIG. 3 in the case of the first embodiment.

The standard current quantity cited here: is the quantity of electric current supplied to each of the fluoroscopic radiation generators 5A and 5B when a three-dimensional position of a target 3 is included in a standard photographing region; and is set at a small value of the extent of being able to compute a two-dimensional position of the target 3.

Further, the reduced current quantity cited here: is the quantity of electric current supplied to each of the fluoroscopic radiation generators 5A and 5B when a three-dimensional position of a target 3 is not included in the standard photographing region; and is set at a value that is smaller than the standard current quantity and is small to the extent of being able to compute a two-dimensional position of the target 3.

Furthermore, when a three-dimensional position of a target 3 is included in the standard photographing region, a step of setting the quantities of electric current supplied to the fluoroscopic radiation generators 5A and 5B at the standard current quantity is carried out in place of Step S104. When a three-dimensional position of a target 3 is not included in the standard photographing region, a step of setting the quantities of electric current supplied to the fluoroscopic radiation generators 5A and 5B at the reduced current quantity is carried out in place of Step S105.

Figure 12:
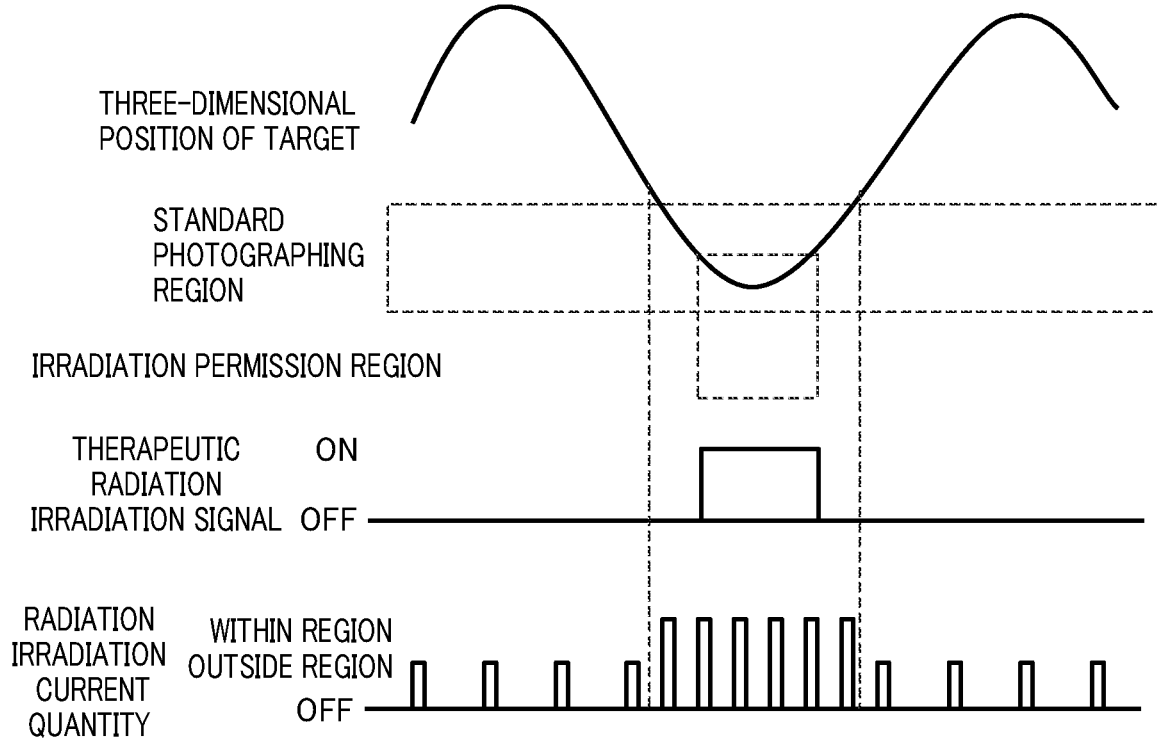
FIG. 12 is a timing chart showing another example of the irradiation signals of a therapeutic particle beam and fluoroscopic radiation and the coordinates of a target according to the first modification of the present invention.

Moreover, in the present first modification, it is possible to change the quantities of electric current and fluoroscopic radiation photographing intervals simultaneously as shown in FIG. 12. By controlling photographing intervals and electric current quantities simultaneously, it is possible to further reduce the loads of the fluoroscopic radiation generators 5A and 5B. FIG. 12 is a timing chart showing the irradiation signals of a therapeutic particle beam and fluoroscopic radiation and the coordinates of a target according to the present first modification.

Here, the control in the present first modification can be applied for any one of the second to fourth modifications that will be explained below.

Second Modification

As a modification of the first to third embodiments, it is possible to: divide a standard photographing region into a plurality of ranges; and change the photographing interval of fluoroscopic radiation stepwise between a standard photographing interval and an expanded photographing interval.

By changing a photographing interval stepwise in this way, it is possible to: more hardly lose sight of a target 3 in the vicinity of an irradiation region; and further reduce the loads of fluoroscopic radiation photographing apparatuses 4A and 4B.

Third Modification

As a modification of the first to third embodiments, a standard photographing region can be disintermediated. In other words, when the quantity of movement of a target 3 is small and a three-dimensional position of the target 3 is stable in a standard photographing region, the target 3 does not get lost and the three-dimensional position can be captured with a high degree of accuracy even when the frequency of measuring the three-dimensional position of the target 3 by fluoroscopic radiation is reduced and hence the standard photographing region can be disintermediated.

By disintermediating a standard photographing region in this way, it is possible to: reduce the loads of fluoroscopic radiation generators 5A and 5B when a three-dimensional position of a target 3 is stable in the standard photographing region; and further reduce the loads of fluoroscopic radiation photographing apparatuses 4A and 4B.

Fourth Modification

As a modification of the fourth embodiment, when a distance between a three-dimensional position of a target 3 and a reference point is not larger than a pre-set specified value, the photographing interval of fluoroscopic radiation can be set so as to be infinite similarly to the third modification.

By such control, the loads of fluoroscopic radiation generators 5A and 5B can be reduced also when a three-dimensional position of a target 3 is stable in the vicinity of a reference point.

Meanwhile, although the explanations have been made on the basis of the case of using a target 3 as a tracking object in the first to fourth embodiments and the first to fourth modifications which are described above, the tracking object is not limited to the target 3. The tracking object can be for example: a marker that is embedded in the vicinity of a target 3, has an arbitrary shape, and includes an arbitrary number of pieces; a high density region in a test object 2, for example a bone such as a rib; or the like.

What is claimed is:
1. A radiation therapy system comprising:
 a therapeutic radiation irradiation apparatus configured to irradiate a therapeutic beam to a target in a subject;
 at least two fluoroscopic radiation photographing apparatuses configured to acquire fluoroscopic images of a tracking object, which is the target, simultaneously from at least two directions by fluoroscopic radiation; and a controller, coupled to the therapeutic radiation irradiation apparatus and the at least two fluoroscopic radiation photographing apparatuses, the controller configured to:

compute a three-dimensional position of the target from fluoroscopic images acquired by the fluoroscopic radiation photographing apparatuses, determine whether the target exists in a predetermined irradiation region based on the computed three-dimensional position of the target and control the therapeutic radiation irradiation apparatus to irradiate the target with the therapeutic beam upon determining the target is judged to exist in the irradiation region, control irradiation dose per unit time of the fluoroscopic radiation photographing apparatuses based on the three-dimensional position of the target, and determine whether the three-dimensional position of the target is included in a standard photographing region, which is a three-dimensional region obtained by expanding or contracting the irradiation region by a predetermined amount, and control the irradiation dose per unit time of the fluoroscopic radiation photographing apparatuses based on whether the three-dimensional position of the target is included in the standard photographing region, wherein the standard photographing region is either three-dimensionally larger or smaller than the irradiation region.

2. The radiation therapy system according to claim 1, wherein the controller is configured to control the irradiation dose per unit time of the fluoroscopic radiation photographing apparatuses based on the computed first three-dimensional position of the tracking object.

3. The radiation therapy system according to claim 2, wherein the controller is configured to:

control photographing intervals of the fluoroscopic radiation photographing apparatuses to be expanded more when the three-dimensional position of the tracking object is determined not to be included in the standard photographing region than when the three-dimensional position of the target is determined to be included in the standard photographing region.

4. The radiation therapy system according to claim 2, wherein the controller is configured to:

determine whether the three-dimensional position of the tracking object is included in the standard photographing region, and control an electric current supplied to the fluoroscopic radiation photographing apparatuses to be smaller when the three-dimensional position of the target is determined not to exist in the predetermined photographing region than when the three-dimensional position of the target is determined to exist in the predetermined photographing region.

5. The radiation therapy system according to claim 4, wherein the predetermined photographing region is disintermediated.

* * * * *